(12) United States Patent
Veasey et al.

US009446202B2

(10) Patent No.: US 9,446,202 B2
(45) Date of Patent: Sep. 20, 2016

(54) DRIVE MECHANISM FOR A DRUG DELIVERY DEVICE AND RESILIENT ELEMENT FOR A DRIVE MECHANISM

(75) Inventors: Robert Veasey, Leamington Spa (GB); Simon Lewis Bilton, Leamington Spa (UA); Christopher Jones, Tewkesbury (GB); Garen Kouyoumjian, Leamington Spa (GB); Catherine Anne MacDonald, Ashby-de-la-Zouch (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1210 days.

(21) Appl. No.: 13/395,599

(22) PCT Filed: Sep. 29, 2010

(86) PCT No.: PCT/EP2010/064389
§ 371 (c)(1),
(2), (4) Date: Jul. 27, 2012

(87) PCT Pub. No.: WO2011/039201
PCT Pub. Date: Apr. 7, 2011

(65) Prior Publication Data
US 2012/0283651 A1 Nov. 8, 2012

(30) Foreign Application Priority Data
Sep. 30, 2009 (EP) ..................................... 09171731

(51) Int. Cl.
*A61M 5/315* (2006.01)
*A61M 5/24* (2006.01)

(52) U.S. Cl.
CPC ....... *A61M 5/31543* (2013.01); *A61M 5/3158* (2013.01); *A61M 5/31555* (2013.01); *A61M5/3156* (2013.01); *A61M 5/31535* (2013.01); *A61M 5/31593* (2013.01); *A61M 2005/2407* (2013.01)

(58) Field of Classification Search
CPC .. A61M 5/286; A61M 5/282; A61M 5/2425; A61M 5/2429; A61M 5/31586
See application file for complete search history.

(56) References Cited

U.S. PATENT DOCUMENTS 4,710,178 A * 12/1987 Henri ................ A61M 5/31581
401/181

FOREIGN PATENT DOCUMENTS

| DE | 10237258 B4 | 9/2006 |
| EP | 0498737 A1 | 8/1992 |
| EP | 1 923 083 A1 * | 5/2008 |
| EP | 1923083 A1 | 5/2008 |
| FR | 2 536 206 A1 * | 5/1984 |
| FR | 2535206 A1 | 5/1984 |

OTHER PUBLICATIONS

Form PCT/IPEA/416, Notification of Transmittal of the International Preliminary Report on Patentability, Jan. 12, 2012.

* cited by examiner

*Primary Examiner* — Kami A Bosworth
*Assistant Examiner* — Matthew A Engel
(74) *Attorney, Agent, or Firm* — McDonnell Boehnen Hulbert & Berghoff LLP

(57) ABSTRACT

A plunger (4) having engaging means and a lever (5) are arranged in a body (1). The lever has a first pivot that is stationary with respect to the body in the direction of an axis, a second pivot, and a third pivot formed by an engaging element of the lever. The pivots are arranged in such a manner that a rotation of the lever with respect to the first pivot moves the second pivot and the third pivot in the same direction with respect to the axis. The engaging element and the engaging means are shaped such that the lever is disengaged from the plunger when the second pivot is moved relatively to the plunger in the proximal direction (30), and the plunger is engaged with the lever when the second pivot is moved in the distal direction (20).

16 Claims, 6 Drawing Sheets

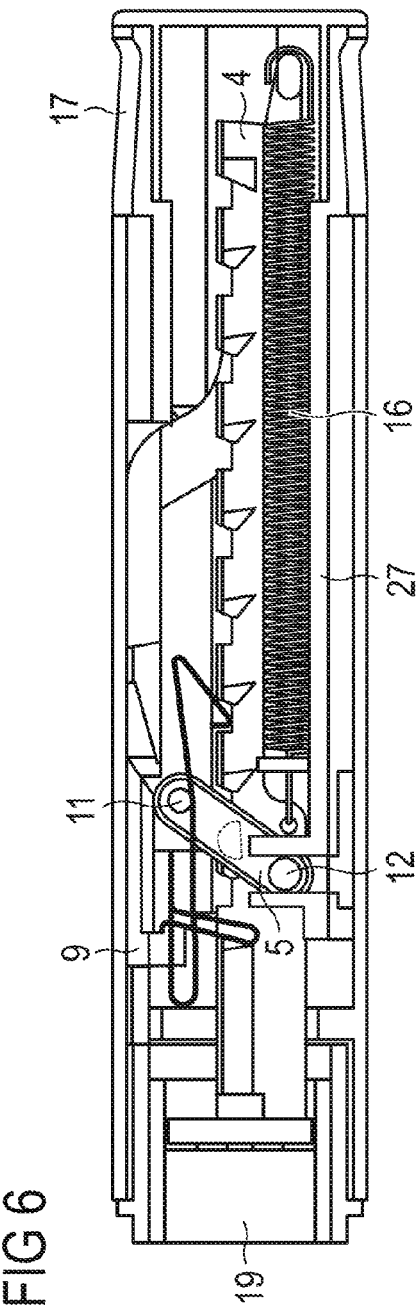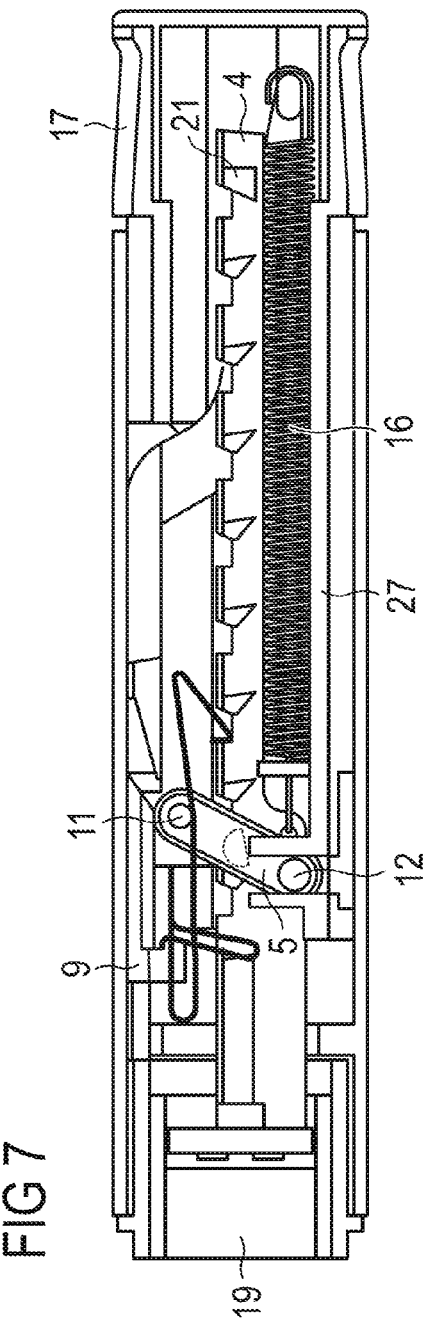

DRIVE MECHANISM FOR A DRUG DELIVERY DEVICE AND RESILIENT ELEMENT FOR A DRIVE MECHANISM

The present invention relates to a drive mechanism for a drug delivery device and a resilient element for such a drive mechanism.

Portable drug delivery devices are used for the administration of a drug that is suitable for self-administration by a patient. A drug delivery device is especially useful in the shape of a pen, which can be handled easily and kept everywhere available. A type of drug delivery device is constructed to be refillable and reusable many times. A drug is delivered by means of a drive mechanism, which may also serve to set the dose or amount to be delivered.

DE 102 37 258 B4 describes a drug delivery device in the shape of an injection pen having a drive mechanism, which allows to deliver a plurality of different prescribed doses. The drive mechanism comprises elements which are rotated relatively to one another around a common axis. They are coupled by unidirectional gears.

It is an object of the present invention to facilitate provision of a new drive mechanism for a drug delivery device.

This object is achieved by a drive mechanism according to claim 1 and the use of a resilient element for a drive mechanism according to claim 12. Further objects are achieved by variants and embodiments according to the dependent claims.

The drive mechanism for a drug delivery device comprises a body having a distal end and a proximal end, which are spaced apart in the direction of an axis. A plunger having engaging means is arranged within the body. A lever is arranged within the body, the lever having a first pivot that is stationary with respect to the body in the direction of the axis, a second pivot, and a third pivot formed by an engaging element of the lever. The pivots are arranged in such a manner that a rotation of the lever with respect to the first pivot moves the second pivot and the third pivot in the same direction with respect to the axis. The engaging element and the engaging means are shaped such that the lever is disengaged from the plunger when the second pivot is moved relatively to the plunger in the proximal direction, and the plunger is engaged with the lever when the second pivot is moved in the distal direction.

The body can be any housing or any component that forms part of a housing, for example. The body can also be some kind of an insert connected with an exterior housing. The body may be designed to enable the safe, correct, and/or easy handling of the device and/or to protect it from harmful liquids, dust or dirt. The body can be unitary or a multipart component of tubular or non-tubular shape. The body may house a cartridge, from which doses of a drug can be dispensed. The body can especially have the shape of an injection pen. The term "distal end" refers to a part of the body or housing which is intended to be arranged at a portion of the drug delivery device from which a drug is dispensed. The term "proximal end" refers to a part of the body or housing which is remote from the distal end.

The term "plunger" encompasses any element that is provided to transfer a movement to a piston, especially for the purpose of dispensing a drug. The plunger may be flexible or not. It may be of unitary or multipart construction, and may especially be a piston rod, a lead screw, a rack-and-pinion, a worm gear system, or the like.

The drive mechanism can be used to expel a drug from a receptacle or cartridge inserted in the body of a drug delivery device. The drug delivery device can be a disposable or re-usable device designed to dispense a dose of a drug, especially a liquid, which may be insulin, a growth hormone, a heparin, or an analogue and/or a derivative thereof, for example. The device can be configured to dispense fixed doses of the drug or variable doses. The drug may be administered by a needle, or the device may be needle-free. The device may be further designed to monitor physiological properties like blood glucose levels, for example.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thrombo-embolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39), des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa. U.S.A., 1985 and in Encyclopedia of Pharmaceutical Technology.

Pharmaceutically acceptable solvates are for example hydrates.

Each time the plunger is shifted in the distal direction with respect to the body, a certain amount of the drug is expelled from the drug delivery device. The drive mechanism is designed such that various doses of the drug to be delivered can be preset. For the setting of a dose, the drive mechanism can be provided with an operation member, called set member in the following. The set member can be provided with a grip on a part which juts out of the body. The grip is used to draw or screw the set member out of the body in the proximal direction. Thus it is possible to turn the lever around the first pivot, the set member functioning as the movable second pivot, and the third pivot of the lever is shifted simultaneously in the proximal direction.

An embodiment of the drive mechanism comprises a resilient element, which acts on the lever and tends to engage the engaging element of the lever with the engaging means of the plunger. Further engaging means are provided on the plunger. The resilient element engages with the further engaging means, thus preventing the plunger from moving in the proximal direction. The resilient element disengages from the further engaging means when the plunger is moved in the distal direction.

In a further embodiment, the resilient element is engaged with the further engaging means when the second pivot is moved in the proximal direction.

In a further embodiment, a movement of the second pivot relative to the plunger in the proximal direction disengages the lever from the plunger and causes a deformation of the resilient element. A force that engages the resilient element with the further engaging means is enhanced by the deformation.

In a further embodiment, the pivots permit a shift of the lever with respect to the body in a direction transverse to the direction of the axis, the lever being disengaged from the plunger by the shift. The shift of the lever can be provided to enable a movement of the plunger relatively to the body in the proximal direction. A release block is arranged at a provided location within the body, where the release block prevents the shift of the lever. The release block is removable from the provided location to enable the lever to be reversibly disengaged from the plunger by the shift.

In a further embodiment, a spring exerts a force on the plunger relatively to the body in the proximal direction. The spring can be provided to reset the plunger to a start position when the lever is permanently disengaged from the plunger by a shift of the lever transverse to the direction of the axis.

A further embodiment comprises a part that is removable from and attachable to the body at the distal end and a resilient element acting on the release block. The release block is kept removed from the provided location by means of the resilient element when the removable and attachable part is not attached to the body. The removable and attachable part of the body can be a cartridge holder, and the release block is held in the provided location when the removable and attachable part is attached to the body with a cartridge inserted. The resilient element which acts on the lever and tends to engage the engaging element with the engaging means, and the resilient element acting on the release block can be a spring member formed from a wire.

A further embodiment comprises a last-dose stop provided on the plunger. The last-dose stop limits the engaging means in the proximal direction and prevents the engaging element from being moved past the last-dose stop.

The drive mechanism may favorably comprise the following operational features. The first pivot of the lever is movable in a direction transverse to the axis. The first pivot is held in its position by a resilient element, which acts on a protruding element of the first pivot, for example. The movement of the plunger in the proximal direction is inhibited, which can be achieved also by the resilient element, which may be provided with a suitable hook or with some other device engaging a provided structure of the plunger. The movement of the lever around the first pivot makes the third pivot, which is formed by an engaging element of the lever, disengage from the corresponding engaging means of the plunger. This is made possible by a short movement of the first pivot transversely to the axis. After the temporary disengagement of the third pivot from the engaging means of the plunger, the lever is again engaged with the plunger. A shift of the set member in the distal direction will then move the lever back into its previous position, and the engaging element of the lever shifts the plunger in the distal direction as well.

The drive mechanism provides a reset function. The plunger is shifted in the distal direction during a delivery operation. This is achieved by the lever being moved when the lever is engaged with the plunger. During a reset operation, the lever is disengaged from the plunger, and the plunger is free to be moved in the proximal direction to a start position. The drive mechanism is thus reset, and the drug delivery device that is equipped with the drive mechanism is ready to be used again. It is thus possible to deliver drugs from a new cartridge or a refilled receptacle in the body.

A resilient element for a drive mechanism of a drug delivery device comprises a resilient or resiliently mounted cantilever with a hook having a sloping profile. The hook is formed in such a fashion that a sawtooth structure that is arranged parallel to the cantilever and moved relatively to the cantilever is either arrested by means of the hook engaging a sawtooth or, depending on the direction of the relative movement, deflects the cantilever by means of the sloping profile sliding over a sawtooth. A section of the cantilever is provided for a lever to act on, the cantilever being deflected by a shift of the lever in a direction transverse to the cantilever.

The resilient element may further comprise a further resilient or resiliently mounted cantilever, the cantilevers having a common mounting and extending into directions that are transverse to one another. The cantilevers can be parts of a spring formed from a wire.

A detailed description of examples of the drive mechanism will be given in the following in conjunction with the appended figures.

FIG. 6 shows a cross-section according to FIG. 5 at the end of the delivery operation.

FIG. 7 shows a cross-section according to FIG. 6 after the release of the mechanism.

Figure 1:
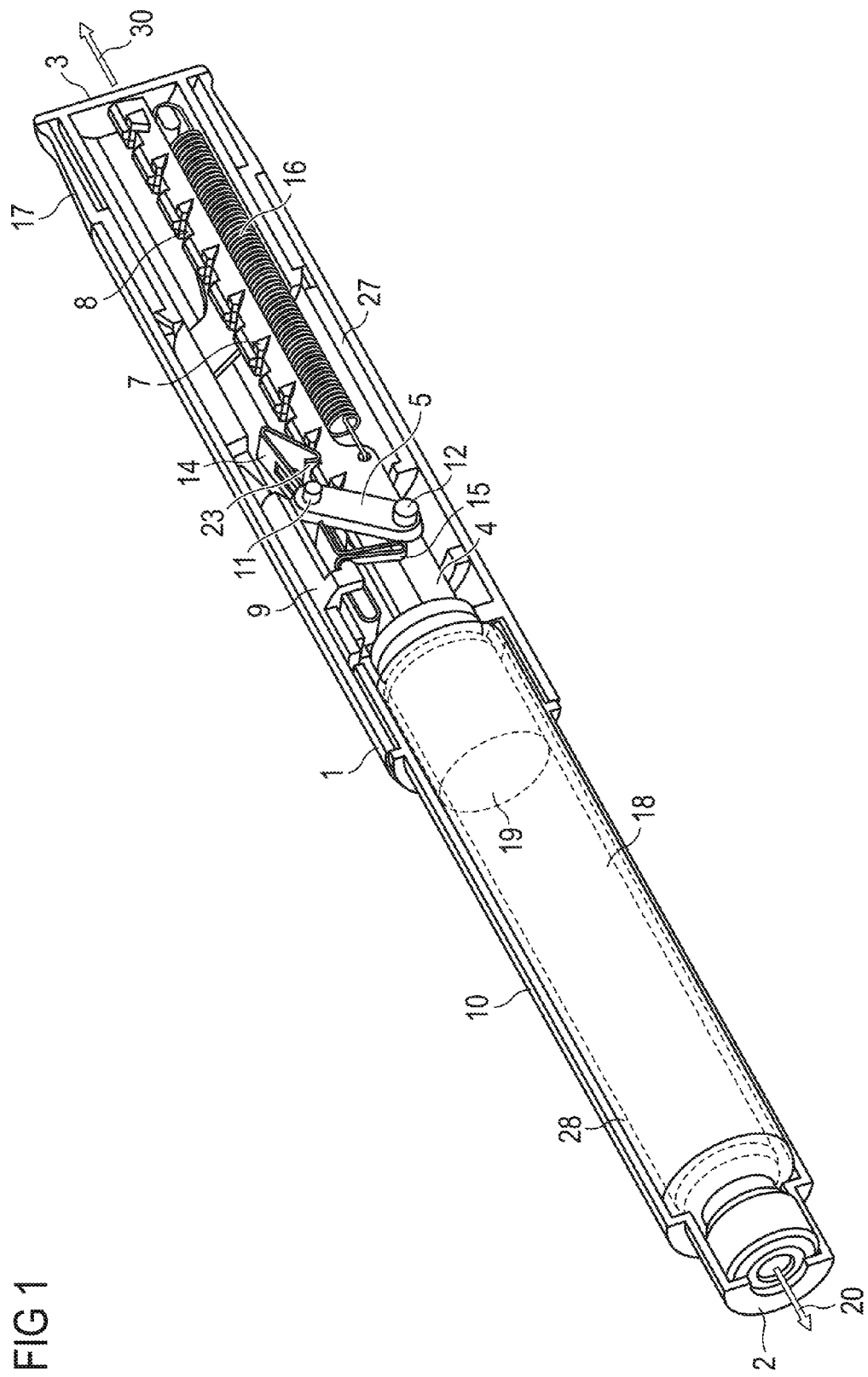
FIG. 1 shows a perspective view of a cross-section of an injection pen comprising the drive mechanism.

FIG. 1 shows a cut-away view of an injection pen comprising the drive mechanism. The injection pen is reusable. The body 1 of the injection pen has a distal end 2 and a proximal end 3. A receptacle 28 for a drug in the body 1 can be refilled, particularly by inserting a new cartridge 18 in the removable and attachable part 10 at the distal end 2. The mechanism is designed to deliver a preset fixed dose of the drug by a movement of the plunger 4 driving a piston 19 in the distal direction 20. A set member 27 forms a moving pivot and is used to set a dose by moving the set member 27 in the proximal direction 30.

In the embodiment shown in FIG. 1, a dose is set by pulling the set member 27 out of the body 1 by means of the grip 17. The lever 5 is turned around its first pivot 11, because the proximal movement of the set member 27 shifts the second pivot 12 of the lever 5 in the proximal direction 30, and the first pivot 11 is stationary in the axial direction with respect to the body 1. The plunger 4 is held in its present position by means of a resilient element 14 engaging corresponding engaging means 7 of the plunger 4, by means of a hook 23, for example. The engagement between the lever 5 and the plunger 4 is therefore temporarily released, and the lever 5 disengages from and reengages with the plunger 4.

Shifting the set member 27 back in the distal direction 20 turns the lever 5 back to its previous position and thus shifts the plunger 4 in the distal direction 20. The means that inhibits a movement of the plunger 4 in the proximal direction 30, during dose setting the hook 23 in the embodiment of FIG. 1, is designed in such a fashion that a movement of the plunger 4 in the distal direction 20 is allowed. A further resilient element 16 can be provided to exert a force on the plunger 4 in the proximal direction 30, thus avoiding an undesired dose inaccuracy that might be caused by a clearance of the mechanism.

A release block 9 can be provided to maintain the lever 5 in a position where it is operable in the described manner. When the removable and attachable part 10, particularly a cartridge holder, is removed, the release block 9 is shifted out of its provided location within the body 1, and the lever 5 is able to move into a position where the engagement with the plunger 4 is permanently released. This allows the plunger 4 to be reset to a start position. When the removable and attachable part 10 is attached to the main part of the body 1, it pushes the release block 9 back to its provided location, thus holding the lever 5 in a position ready for operation. The reset of the plunger 4 can be facilitated by means of a resilient element 16 acting as a plunger return spring. The set, deliver and reset operations will be described in more detail in the following.

Figure 2:
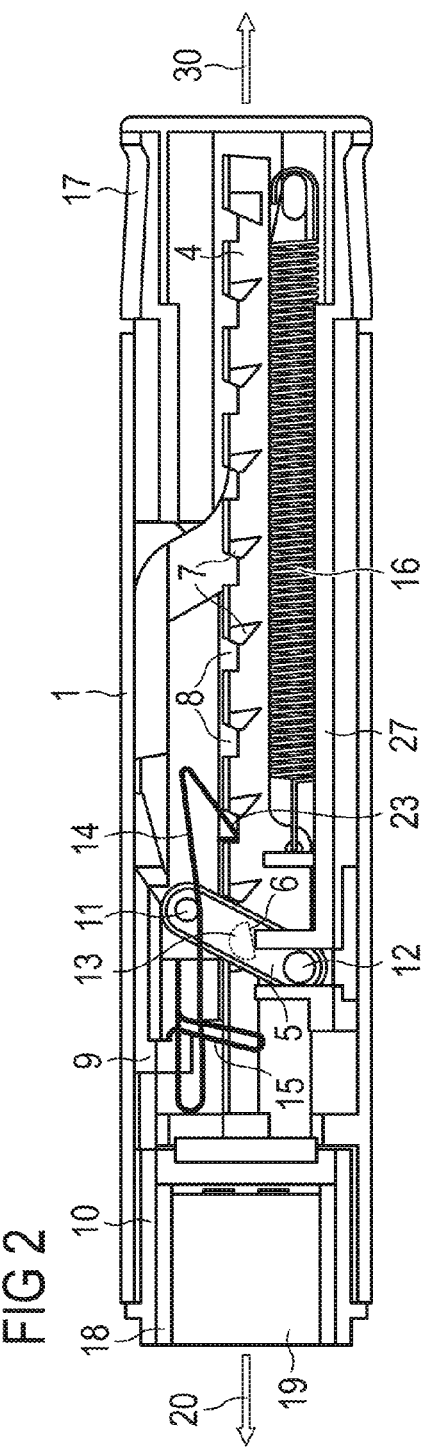
FIG. 2 shows a cross-section of an embodiment of the drive mechanism in a start position.

FIG. 2 shows a cross-section of an embodiment of the drive mechanism in the state preceding a set operation. A cartridge 18 containing a piston 19 for the drug delivery is shown to be inserted in the removable and attachable part 10 at the distal end on the left side of FIG. 2. The piston 19 is moved in the distal direction 20, to the left in FIG. 2, by a corresponding shift of the plunger 4. The plunger 4 has engaging means 7 facing the lever 5 and further engaging means 8 forming a saw tooth structure on an upper rim of the plunger 4. The plunger 4 can be shifted in the axial direction with respect to the body 1. The set member 27, which can be formed of one integral part or of several assembled parts, is shown to jut out of the body 1 on the right-hand side of FIG. 2, where the set member 27 comprises a grip 17 for the operation by a user. The set member 27 forms a moving pivot, which is shifted in the proximal direction 30 and coincides with the second pivot 12 of the lever 5.

The lever 5 comprises a first pivot 11 which is stationary in the axial direction and movable transversely to the axial direction. The second pivot 12 forms the moving pivot, and a third pivot 13 is formed by an engaging element 6 coupled with the engaging means 7 of the plunger 4. The first pivot 11 is a cylindrical axis in this embodiment, the second pivot 12 is a flat cylindrical protruding element on the side of the lever 5, and the third pivot 13 is formed by a flat protruding element 6 in the shape of a half cylinder on the side of the lever 5 facing the plunger 4. The engaging means 7 of the plunger 4 can be formed by protruding elements, which may have the shape of a series of teeth, for example.

The resilient element 14 which keeps the lever 5 in its position with respect to the direction transverse to the axis of the body 1 is provided with a hook 23 or spike engaging the further engaging means 8 of the plunger 4 and holding the plunger 4 in its position. A movement of the first pivot 11 in the direction to the neighboring inner surface of the body 1 is inhibited by a release block 9. The second pivot 12 of the lever 5 is coupled with the set member 27 such that a shift of the set member 27 shifts the second pivot 12 and turns the lever 5 around the first pivot 11. This movement simultaneously shifts the third pivot 13, which is formed by the engaging element 6 that is engaged with the engaging means 7 of the plunger 4.

Figure 3:
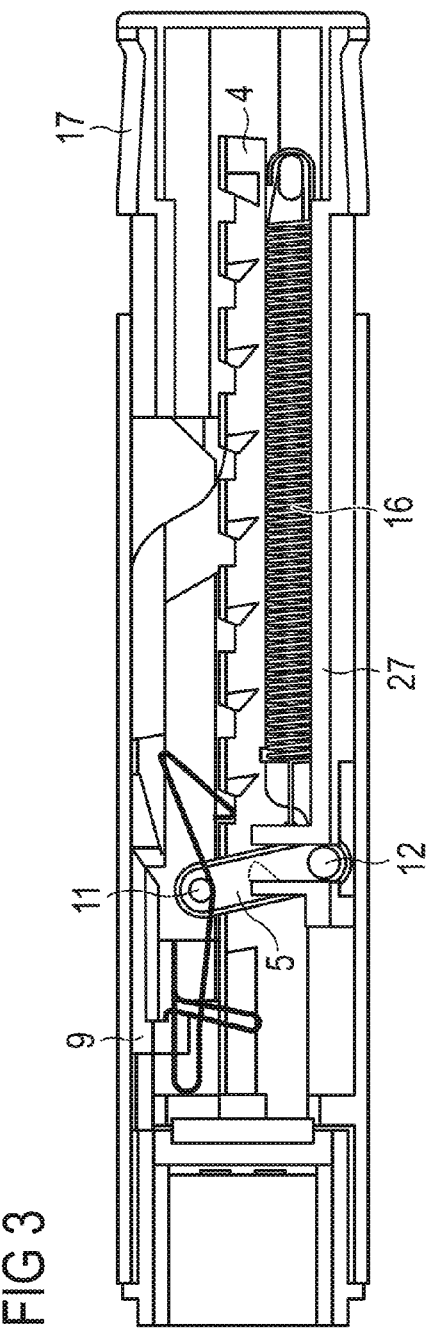
FIG. 3 shows a cross-section according to FIG. 2 during a set operation.

FIG. 3 shows a cross-section according to FIG. 2 during a set operation. To set a dose, the user pulls the set member 27, thus rotating the lever 5 around the first pivot 11. As the plunger 4 is not able to move in the proximal direction 30, the engaging element 6 of the lever 5 disengages from the engaging means 7 of the plunger 4, and the lever 5 is not only rotated, but additionally shifted transversely to the axis of the body 1 away from the position of the release block 9. This movement is achieved against the force of the resilient element 14. After the engaging means 7 of the plunger 4 has thus been overridden by the engaging element 6 of the lever 5, the resilient element 14 forces the first pivot 11 of the lever 5 back into its previous position, and the engaging element 6 of the lever 5 reengages with the engaging means 7 of the plunger 4 by entering an intermediate space between the protruding elements forming the engaging means 7.

The shape of the resilient element 14 shown in FIG. 3 has the advantage that the shift of the lever 5 against the action of the resilient element 14 strengthens the engagement of the resilient element 14 with the further engaging means 8 of the plunger 4, thus strongly inhibiting the shift of the plunger 4 in the proximal direction 30.

Figure 4:
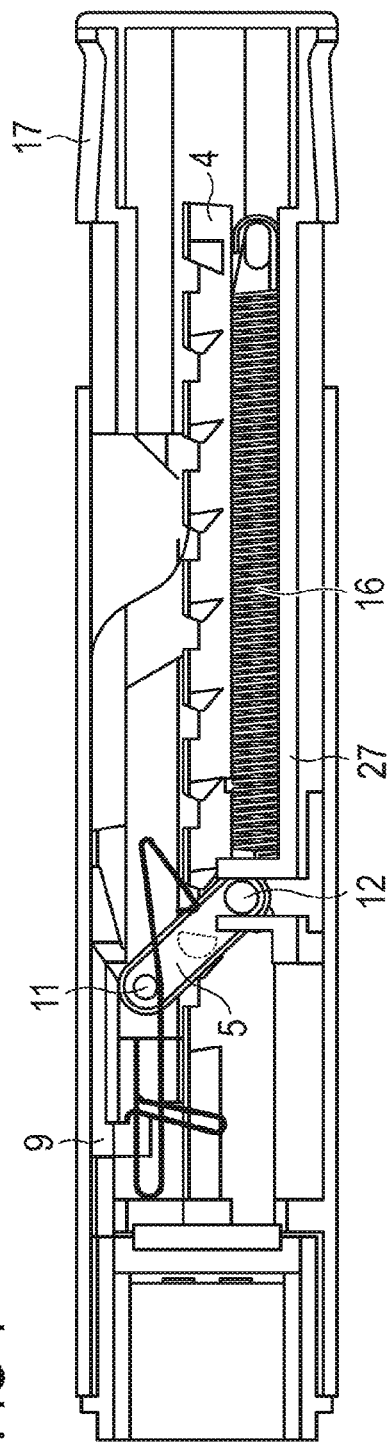
FIG. 4 shows a cross-section according to FIG. 3 after the set operation.

FIG. 4 shows a cross-section according to FIG. 3 when the set operation has been finished. The set member 27 is fully out and the lever 5 is fully rotated. The lever 5 is pushed against the release block 9 by the resilient element 14.

Figure 5:
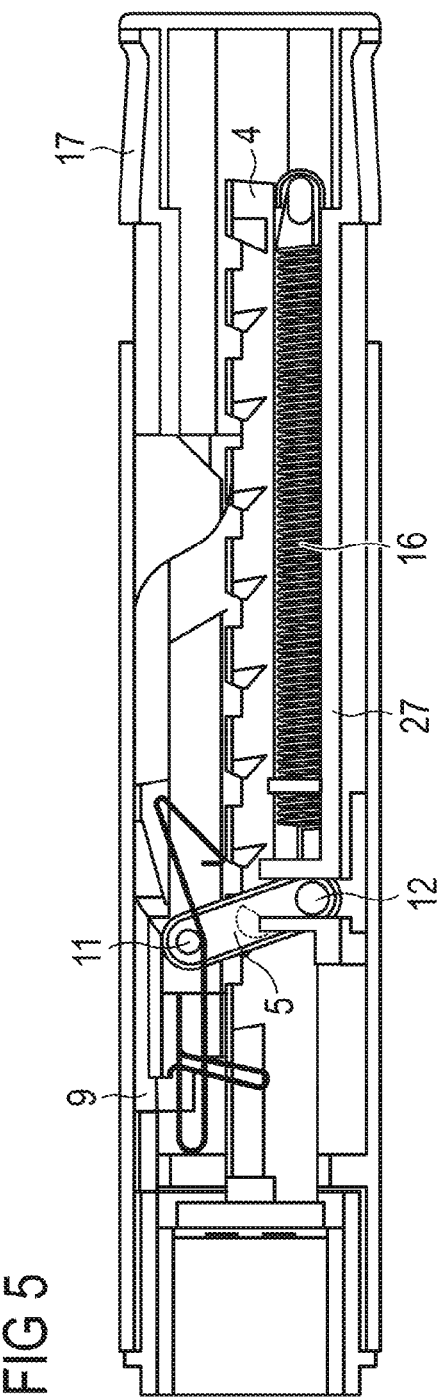
FIG. 5 shows a cross-section according to FIG. 4 during a delivery operation.

FIG. 5 shows a cross-section according to FIG. 4 during a delivery operation. The user pushes the set member 27 in the distal direction 20. The coupling between the set member 27 and the second pivot 12 of the lever 5 rotates the lever 5 around its first pivot 11. The third pivot 13 is also pushed in the distal direction 20, and so is the plunger 4 because of the engagement between the engaging element 6 of the lever 5 and the engaging means 7 of the plunger 4. The plunger 4 advances in the distal direction 20 to dispense the set dose of the drug. The hook 23 of the resilient element 14 rides out of the further engaging means 8 of the plunger 4, and the load of the resilient element 14 is again increased in order to keep the lever 5 in contact with the release block 9. This ensures the engagement between the lever 5 and the plunger 4 during the delivery operation. Because the lever 5 does not disengage from the plunger 4, the plunger 4 is shifted in the distal direction 20 while the lever 5 is being turned around its first pivot 11. Thus the full dose corresponding to the distance between two elements of the engaging means 7 of the plunger 4 is delivered.

FIG. 6 shows a cross-section according to FIG. 5 at the end of the delivery operation, when the set member 27 is in its farthest position in the distal direction 20. A comparison of FIG. 6 with FIG. 2 shows that the plunger 4 has now been shifted by a certain distance in the distal direction 20.

The embodiment of the drive mechanism shown in the figures is provided with a further resilient element 16 acting as a plunger return spring and exerting a force on the plunger 4 in the proximal direction 30 with respect to the body 1. When the set member 27 is released by the user after the drug delivery, this resilient element 16 pulls the plunger 4 in the proximal direction 30, until the hook 23 of the resilient element 14 acting on the lever 5 engages with the further engaging means 8 of the plunger 4 and thereby stops the movement of the plunger 4 in the proximal direction 30. As the lever 5 is slightly turned during this procedure, the set member 27 is moved accordingly by a small distance in the proximal direction 30, as indicated in FIG. 7. The plunger 4 then occupies a well-defined start position irrespective of a possible clearance of the mechanical parts of the drive mechanism. This is a back-off feature, which is favorable in view of dose accuracy, because the resilient element 16 prevents the plunger 4 from moving in the distal direction 20 during a set operation, before the user pushes the set member 27 in the distal direction 20 to deliver the set dose. Without having a plunger return spring, post-dispense back-off can be achieved by alternative means, for instance by a plastic spring molded as part of the first pivot 11 or the second pivot 12, or set member or body or release block. Instead, an additional feature of the resilient element 14 acting on the lever 5 may be provided to act on the second pivot 12.

The described sequence of operations is repeated until the prescribed number of doses have been dispensed. To prevent the drive mechanism from being set after the last dose has been dispensed, a stop feature can be provided on the plunger 4. The stop feature captures the third pivot 13 of the lever 5 and inhibits the movement of the lever 5, thus preventing a shift of the set member 27 in the proximal direction 30. The feature is a last-dose stop 21 in the embodiment shown in the figures. The last-dose stop 21 is provided by the last protruding element of the engaging means 7 of the plunger 4 being formed such that the engaging element 6 of the lever 5 is not able to override this protruding element when the set member 27 is pulled in the proximal direction 30.

Figure 8:
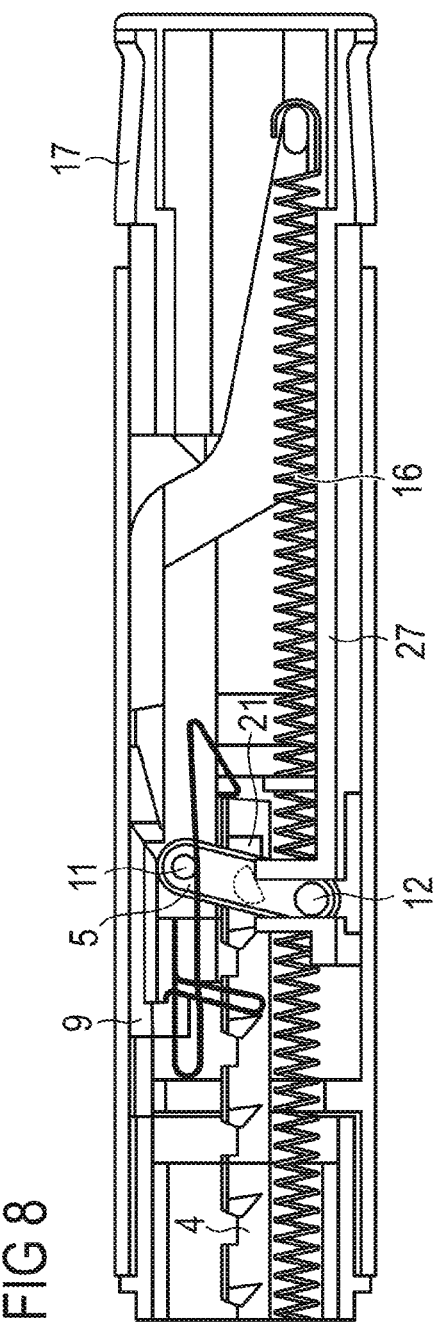
FIG. 8 shows a cross-section according to FIG. 7 in a last-dose position.

FIG. 8 shows a cross-section of the drive mechanism after the last dose has been dispensed and the engaging element 6 of the lever 5 is stopped at the last-dose stop 21. Now it is not possible to pull the set member 27 in the proximal direction 30 farther than to the position shown schematically in FIG. 8.

Figure 9:
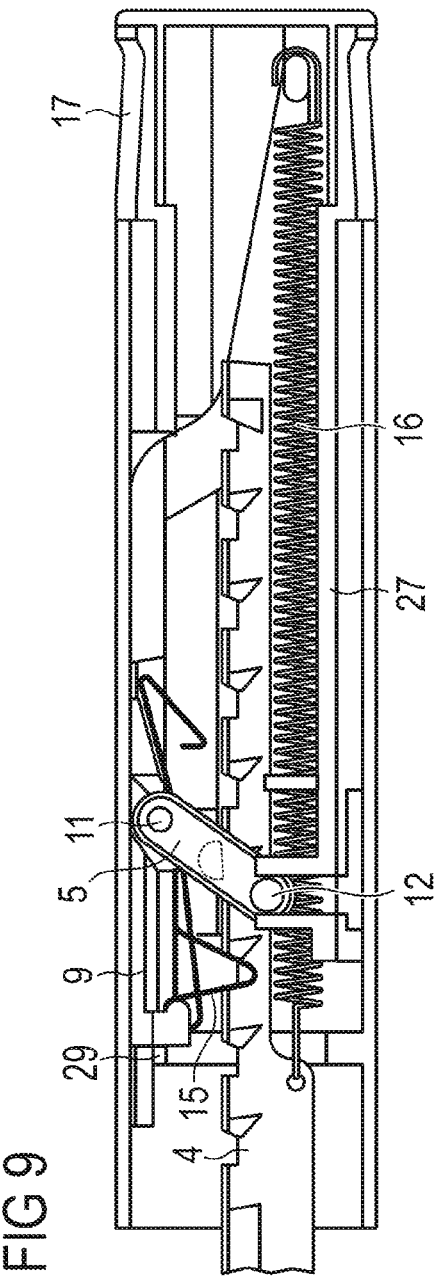
FIG. 9 shows a cross-section according to FIG. 8 after the removal of the cartridge holder.

A reset operation of the drive mechanism will now be described with reference to FIGS. 9 and 10. When the receptacle 28 of the body 1 or the cartridge 18 is empty, the user removes the removable and attachable part 10, particularly a cartridge holder, from the main part of the body 1. The cross-section of FIG. 9 shows the body 1 after this part 10 has been removed and the release block 9 has been shifted from its provided location. The shift of the release block 9 is achieved by the action of a further resilient element 15. Stop means like the web 29 or interface of the body 1 shown in the cross-section of FIG. 9 is provided to prevent the release block 9 from being shifted completely out of the body 1. It suffices if the release block 9 releases the lever 5 from its position where it is engaged with a plunger 4. The resilient element 14 helps to move the lever 5 transversely to the axis of the body 1 towards the inner sidewall of the body 1, so that the engaging element 6 of the lever 5 is disengaged from the engaging means 7 of the plunger 4, and the plunger 4 is free to move axially with respect to the body 1. This allows the user to push the plunger 4 back to its start position at the proximal end 3 of the body 1 or the plunger return spring 16 to pull the plunger 4 accordingly.

Figure 10:
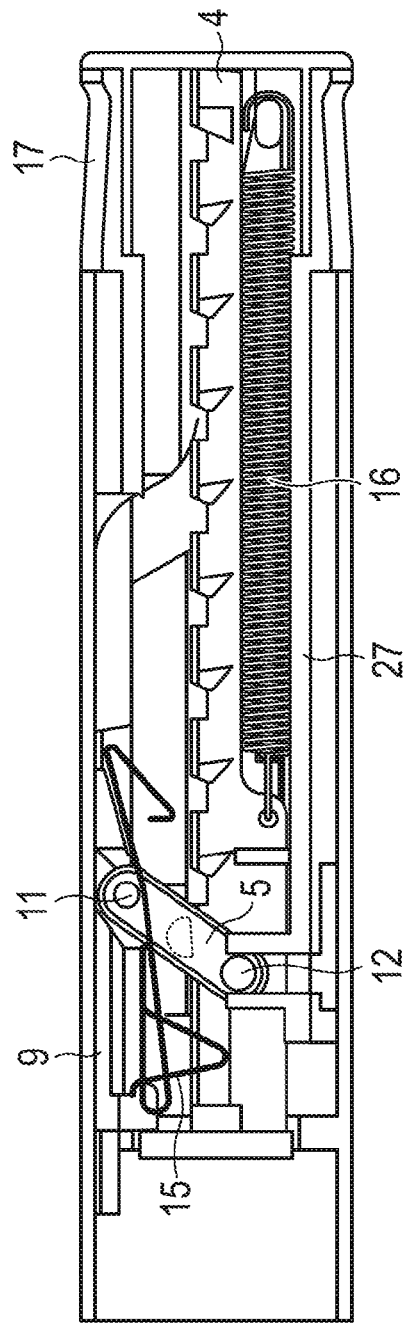
FIG. 10 shows a cross-section according to FIG. 9 after a reset operation.

FIG. 10 shows the arrangement of the drive mechanism after the reset operation with the plunger 4 occupying its start position at the proximal end 3 of the body 1. The removed part 10 can now be attached, preferably with a new cartridge 18 inserted, and the release block 9 is shifted back to its provided location, where it holds the lever 5 in a position of engagement with the plunger 4. Then the drive mechanism is in its start state according to the cross-section of FIG. 2.

Figure 11:
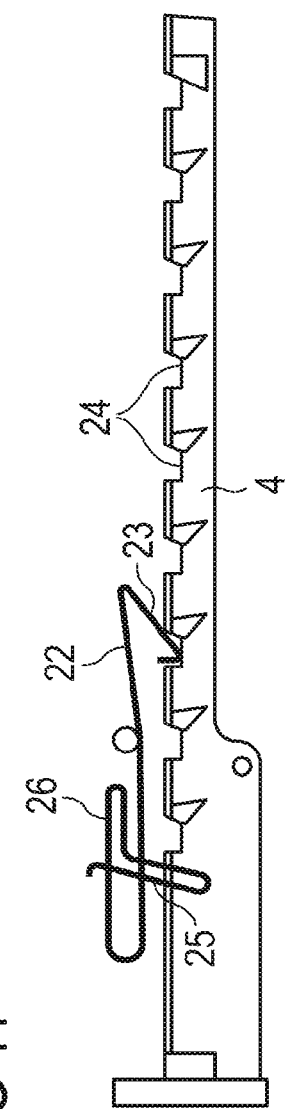
FIG. 11 shows an example of a spring wire forming a resilient element of the mechanism.

FIG. 11 shows an example of a spring wire that can be used as the resilient elements 14, 15 acting on the lever 5 and on the release block 9. The spring according to FIG. 11 comprises a part in the form of a cantilever 22 having a hook 23 at its end, the cantilever 22 providing the resilient element 14 according to FIGS. 1 and 2. The hook 23 is provided to engage with the sawtooth structure 24 forming the further engaging means 8 of the plunger 4. A further cantilever 25 is provided as the resilient element 15 acting on the release block 9. Both cantilevers 22, 25 can be formed from one strip of wire and fixed relatively to the body 1 by means of a mounting 26. Instead of using a wire, the spring in the shape shown in FIG. 11 can be manufactured as a plastic spring, metal pressing or the like.

The drive mechanism can be used in a drug delivery device intended to deliver fixed doses of a drug. The mechanism allows a reset, so that a cartridge can be replaced and the device reused multiple times. The drive mechanism provides simple pull-push user operation. A dose is set by pulling a dose button out of a body and is injected by pushing the button back to its starting position. The drive mechanism has a mechanical advantage with a high efficiency and enables a design whereby the engagement of the lever and the plunger provides audible and/or tactile feedback both on setting and delivering of each dose. The drive mechanism can especially be used within a pen injector as shown in FIG. 1, for example, for the delivery of fixed doses of a drug into the body by means of a needle. It may especially be used for the delivery of a range of fluid medicaments. The drive mechanism has relatively low part count and is particularly attractive for cost-sensitive device applications.

REFERENCE NUMERALS 1 body
2 distal end
3 proximal end
4 plunger
5 lever
6 engaging element of the lever
7 engaging means of the plunger
8 further engaging means of the plunger
9 release block
10 removable and attachable part
11 first pivot
12 second pivot
13 third pivot
14 resilient element
15 resilient element
16 resilient element
17 grip
18 cartridge
19 piston
20 distal direction
21 last-dose stop
22 cantilever
23 hook
24 sawtooth structure
25 further cantilever
26 mounting
27 set member
28 receptacle
29 web
30 proximal direction

The invention claimed is:
1. A drive mechanism for a drug delivery device, comprising:

a body having a distal end and a proximal end, which are spaced apart in the direction of an axis, a plunger arranged within the body, the plunger having a first engaging portion and a second engaging portion, the first engaging portion including a plurality of protruding elements, the second engaging portion including a sawtooth structure, a lever arranged within the body, the lever having a first pivot that is stationary with respect to the body in the direction of the axis, a second pivot, and a third pivot formed by an engaging element of the lever, wherein the first, second, and third pivots are arranged such that a rotation of the lever with respect to the first pivot moves the second pivot and the third pivot in a same direction with respect to the axis, wherein the engaging element and the first engaging portion are shaped such that the lever is disengaged from the plunger when the second pivot is moved relatively to the plunger in a proximal direction toward the proximal end, and the plunger is engaged with the lever when the second pivot is moved in a distal direction toward the distal end, and a first resilient element having a cantilever portion, the cantilever portion including a hook having a sloping profile, wherein the cantilever portion engages the lever to bias the engaging element towards engagement with the first engaging portion, and wherein the hook of the first resilient element engages with a sawtooth of the sawtooth structure, thus inhibiting the plunger from moving in the proximal direction, wherein the first resilient element is configured to disengage from the second engaging portion, by deflecting the cantilever portion such that the sloping profile slides over the sawtooth, when the plunger is moved in the distal direction, and wherein the first resilient element is engaged with the second engaging portion when the second pivot is moved in the proximal direction.

2. The drive mechanism according to claim 1, wherein a movement of the second pivot relatively to the plunger in the proximal direction, the movement disengaging the lever from the plunger, causes a deformation of the first resilient element, and a force engaging the hook of the first resilient element with the sawtooth of the sawtooth structure is increased by the deformation.

3. The drive mechanism according to claim 1, further comprising: a second resilient element exerting a force on the plunger relatively to the body in the proximal direction.

4. The drive mechanism according to claim 1, further comprising:
the pivots permitting a shift of the lever with respect to the body in a direction transverse to the direction of the axis, the lever being disengaged from the plunger by the shift,
a release block arranged at a provided location within the body, where the release block prevents the shift of the lever, and
the release block being removable from the provided location to enable the lever to be reversibly disengaged from the plunger by the shift.

5. The drive mechanism according to claim 4, wherein the shift of the lever enables a movement of the plunger relatively to the body in the proximal direction.

6. The drive mechanism according to claim 5, further comprising: a second resilient element exerting a force on the plunger relatively to the body in the proximal direction, the second resilient element resetting the plunger to a start position when the lever is permanently disengaged from the plunger by the shift.

7. The drive mechanism according to claim 4, further comprising:
a removable and attachable part removable from and attachable to the body at the distal end, and
a third resilient element acting on the release block, the release block being kept removed from the provided location via the third resilient element when the removable and attachable part is not attached to the body.

8. The drive mechanism according to claim 7, wherein the removable and attachable part of the body is a cartridge holder, and the release block is held in the provided location when the removable and attachable part is attached to the body with a cartridge inserted.

9. The drive mechanism according to claim 7, wherein the first resilient element and the third resilient element are a spring member formed from a wire.

10. The drive mechanism according to claim 1, further comprising:
a last-dose stop provided on the plunger,
the last-dose stop limiting the first engaging portion in the proximal direction and preventing the engaging element from being moved past the last-dose stop.

11. The drive mechanism according to claim 1, wherein a section of the cantilever portion is configured for the lever to act on, and the cantilever portion is deflected by a shift of the lever in a direction transverse to the cantilever portion.

12. The drive mechanism according to claim 11, wherein the resilient element further comprises a second cantilever portion, the first cantilever portion and the second cantilever portion having a common mounting, and
the first cantilever portion and the second cantilever portion extending into directions that are transverse to one another.

13. The drive mechanism according to claim 12, wherein the second cantilever portion is a part of a spring formed from a wire.

14. The drive mechanism according to claim 1, wherein the engaging element has a half cylinder shape.

15. The drive mechanism according to claim 14, wherein the engaging element is located on a side of the lever facing the plunger.

16. The drive mechanism according to 15, wherein the engaging element is located between the first pivot and the second pivot, the first engaging portion is located on a first side of the plunger facing the lever, and the second engaging portion is located on a second side of the plunger adjacent to the first side of the plunger.

* * * * *